United States Patent
Fehr

[11] Patent Number: 5,962,706
[45] Date of Patent: Oct. 5, 1999

[54] EPOXIDES, PROCESS FOR THEIR PREPARATION AND THEIR USE FOR THE PREPARATION OF PERFUMING INGREDIENTS

[75] Inventor: Charles Fehr, Versoix, Switzerland

[73] Assignee: Firmenich SA, Geneva, Switzerland

[21] Appl. No.: 08/960,203

[22] Filed: Oct. 29, 1997

[30] Foreign Application Priority Data

Nov. 7, 1996 [CH] Switzerland ............... 2750/96

[51] Int. Cl.⁶ .................................. C07D 303/00
[52] U.S. Cl. ........................................... 549/512
[58] Field of Search ............................. 549/512

[56] References Cited

FOREIGN PATENT DOCUMENTS 4419746  12/1995  Germany .
WO 95/33735  12/1995  WIPO .

OTHER PUBLICATIONS

E.J. Corey et al., "Enantioselective Route to a Key Intermediate in the Total Synthesis of Ginkgolide B", *Tetrahedron Letters*, vol. 29, No. 26 (1988), pp. 3201–3204.

D. Curran et al., "Radical–Initiated Polyolefinic Cyclizations in Linear Triquinane Synthesis. Model Studies and Total Synthesis of (±)–Hirsutene", *Tetrahedron*, vol.41, No. 19 (1985), pp. 3943–3958.

T. Kitahara et al., "A Simple and Efficient Synthesis of (±)–Methyl Dihydroepijasmonate", *Agric. Biol. Chem.*, vol. 50, No. 7 (1986), pp. 1867–1872.

T. Kitahara et al., "Synthesis of (±)–Methyl Epijasmonate and (±)–Methyl Cucurbate", *Agric. Biol. Chem.*, vol. 51, No. 4 (1987), pp. 1129–1133.

*Primary Examiner*—Amelia Owens
*Attorney, Agent, or Firm*—Pennie & Edmonds LLP

[57] ABSTRACT

Epoxides of formula

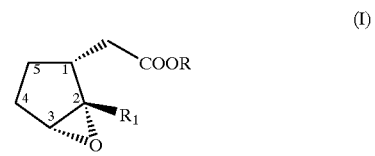

(I)

having a cyclanic (1R) configuration, the group in position 2 being in a trans configuration and the epoxy group being in a cis configuration with respect to that in position 1 of the ring, and in which R represents a lower alkyl group and $R^1$ represents a saturated or unsaturated, linear or branched hydrocarbon group having from 1 to 8 carbon atoms, are useful molecules for the preparation of very prized perfuming ingredients. A process for the preparation of the opoxides (I) is also described.

10 Claims, No Drawings

EPOXIDES, PROCESS FOR THEIR PREPARATION AND THEIR USE FOR THE PREPARATION OF PERFUMING INGREDIENTS

The new epoxides of formula

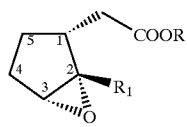
(I)

having a cyclanic (1R) configuration, the group in position 2 being in a trans configuration and the epoxy group being in a cis configuration with respect to that in position 1 of the ring, and in which R represents a lower alkyl group and $R^1$ represents a saturated or unsaturated, linear or branched hydrocarbon group having from 1 to 8 carbon atoms, are useful molecules for the preparation of very prized perfuming ingredients.

An original process for the preparation of the epoxides (I) is also described.

BRIEF SUMMARY OF THE INVENTION

The present invention concerns the field of organic synthesis. More particularly, it concerns epoxides which are useful as starting products for the preparation of highly prized perfuming ingredients, amongst which the isomers of Hedione® (methyl-3-oxo-2-pentyl-1-cyclopentaneacetate; origin: Firmenich SA, Geneva, Switzerland) which are preferred from an olfactive point of view.

Thus, an object of the present invention is an epoxide of formula

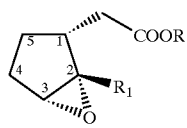
(I)

having a cyclanic (1R) configuration, the group in position 2 being in a trans configuration and the epoxy group being in a cis configuration with respect to that in position 1 of the ring, and in which R represents a lower alkyl group and $R^1$ represents a saturated or unsaturated, linear or branched hydrocarbon group having from 1 to 8 carbon atoms.

By lower alkyl group it is meant here a linear or branched alkyl group from $C_1$ to $C_4$, and more particularly a methyl or ethyl group.

The structure of the epoxides of formula (I) is novel.

PRIOR ART

International patent application WO 95/33735, published on Dec. 14, 1995, describes epoxides of formula

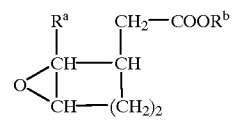
(A)

in which $R^a$ stands for an alkyl group having from 1 to 8 carbon atoms and $R^b$ for an alkyl group from $C_1$ to $C_4$. However, one cannot detect therefrom a description or any mention of the precise stereochemistry of compounds (A). Now, trying to reproduce the process described in this document for the preparation of these compounds, we have discovered that it only allows the preparation of a mixture of diastereomers of each epoxide of formula (A), namely in the cases in which $R^a$ is a pentyl or hexyl group and $R^b$ a methyl or ethyl group. We have thus found that the process for the preparation of epoxides (A) as described in WO 95/33735 is not diastereoselective and that, moreover, the reaction occurs with very low conversion, of the order of 25%.

We have also discovered that, contrary to what is indicated in WO 95/33735, the transformation of the thus-obtained epoxide, under the described reaction conditions, namely the thermal treatment of the epoxicle in presence of a catalytic amount of lithium iodide, leads to the formation of a product which is totally distinct from the desired ketone. So, when applying the process as described in WO 95/33735 to the epoxide of formula (A) wherein $R^a$=pentyl and $R^b$=$CH_3$, we obtained, instead of methyl-3-oxo-2-pentyl-1-cyclopentaneacetate as expected according to the description in the said document, a totally different lactone which was identified by its spectral data as having the structure

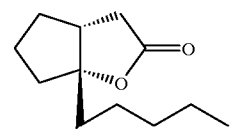

i.e. cis-perhydro-6a-pentyl-2-cyclopenta[b]furanone.

It is in fact a lactone which has been known in our laboratories for a long time, possessing a watery-metallic, chemical odor, which is slightly animal. However, not even a trace of the desired cyclic ketone could be detected in this product. The same applied to the cases where $R^a$=hexyl and $R^b$=methyl or ethyl.

In summary, is apparent from the above that the above-mentioned prior art document does not describe a process which allows either to obtain or to convert the epoxides of formula (I) according to the present invention and that as a result there was no recognition of any particular usefulness of the compounds which are the object of the present invention and have the specific stereochemistry indicated above.

Yet, we have now discovered that compounds (I) are very useful as starting products for the preparation, in a pure state, of optically active perfuming ingredients which are particularly prized by the perfumers.

DETAILED DESCRIPTION OF THE INVENTION

It should also be noticed that, as will be apparent from the comparative examples presented further on, the above-mentioned prior art document does not describe the pure racemates corresponding to epoxides (I), i.e. the epoxides corresponding to the formula

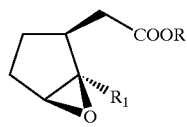
(I')

in which the epoxy and carboxy substituents have a relative configuration which is strictly cis and the symbols R et $R^1$ have the meaning given in formula (I). These compounds, which are equimolar mixtures of an epoxide (I) with its respective enantiomer, are also novel compounds. They turn out to be useful for the preparation of the corresponding ketones having a strictly cis cyclanic configuration and the most interesting example of which, in perfumery, is cis-Hedione® or cis-methyl-3-oxo-2-pentyl-1-cyclopentaneacetate.

According to the invention, the optically active epoxides of formula (I) are preferred compounds and one can cite, as an even more preferred compound, (+)-methyl (1R,2S,3R)-2,3-epoxy-2-pentyl-1-cyclopentaneacetate. The transformation of this compound according to the original process described hereinafter allows the preparation of (+)-cis-Hedione®, or (+)-methyl (1R)-cis-3-oxo-2-pentyl-1-cyclopentaneacetate, i.e. the isomer which is known to possess at best the typical odor characteristics, in particular the jasmine note, of this well-known cyclic ketone.

Therefore, the invention also concerns the use of epoxides of formula (I) for the preparation of cyclic ketones according to the formula

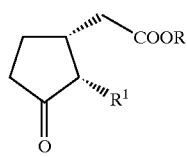
(II)

having a (1R)-cis cyclanic configuration, according to an original conversion process, comprising the treatment of said epoxide in an inert organic solvent with an acidic agent consisting of an appropriate Lewis acid or an acidic clay.

We have discovered with surprise that these reaction conditions made it possible to obtain the optically active ketones of formula (II) in a selective way and excellent yields, as will be apparent from the examples below. This result is contrary to what could be observed with the prior art process as described in the above-cited document, according to which the epoxide was subjected to a thermal treatment in the presence of a salt of an alkaline or alkaline earth metal of an acid of low molecular weight.

The reaction which characterizes the process of the invention is executed at various temperatures which depend on the reagents used and in particular on the reactivity of the acidic agent. Therefore, and contrary to the process described in WO 95/33735, the process of the invention allows the use of mild temperature conditions, typically below 120° C.

As Lewis acids which are appropriate for the process of the invention, one can cite in particular boron trifluoride, which may be complexated (as etherate, for example), aluminum trichloride and magnesium iodide.

As acidic clays, one can use aluminosilicate based clays from the family of products known under the name of FILTROL® (origin: Harshaw/Filtrol), clays which are commercially available under designations like GK (origin: Georgia Kaolin Co.), montmorillonites known under the name of K catalysts, for example K10, KP10, KSF et KSF/O (origin: Süd-Chemie AG), bentonites, or yet any other acidic clay of current use. According to a preferred embodiment of the invention, one will use, for example, Filtrol®G24.

The proportion in which the acidic agent can be used relative to the starting epoxide varies within a large range of concentrations. We have observed that the ratio between the two reagents could be stoichiometric for example, but equally useful results were obtained with catalytic amounts of acidic agent relative to the epoxide.

As solvents which can be used according to the invention, one can employ a solvent of current use which is inert under the reaction conditions. One can cite in particular cyclic or acyclic hydrocarbons, in particular cyclohexane, xylene and toluene, ethers like diethyl ether or tetrahydrofurane, or even chlorinated solvents, in particular dichloromethane. Particularly useful results were obtained with toluene or dichloromethane.

According to a preferred embodiment of the process of the invention, (+)-methyl (1R,2S,3R)-2,3-epoxy-2-pentyl-1-cyclopentaneacetate is used. This embodiment revealed itself particularly advantageous, since, as is cited above, it allows the preparation of the preferred isomer of Hedione®, namely the (+)-methyl (1R)-cis-3-oxo-2-pentyl-1-cyclopentaneacetate.

Of course, when using in the above-described process a racemic epoxide of formula (I') as defined above, the corresponding racemic cyclic ketones will be obtained, which are the racemic equivalents, having a strictly cis cyclanic configuration, of the ketones of formula (II). Thus, when using for example methyl c-2,3-epoxy-2-pentyl-r-1-cyclopentaneacetate, racemic cis-Hedione® will be obtained in a pure state.

The invention also concerns a process for the preparation of epoxides of formula (I) previously defined, characterized in that an ester of formula

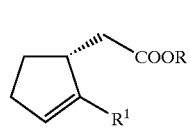
(III)

having a cyclanic (1R) configuration and wherein symbols R and. $R^1$ have the meaning indicated in formula (I), is reacted with a strong peracid in an inert organic solvent.

The optically active esters of formula (III) are novel compounds, prepared according to an original process which will be described further on.

In fact, even though the racemic methyl 2-pentyl-2-cyclopentene-1-acetate is known from the article of T. Kitahara et al., in Agric. Biol. Chem. 50, 1867 (1986), there is no mention in this article of one or the other of the enantiomers which are present in this racemic compound, namely that of (1R) configuration which obeys formula (III). Now, as will be seen further on, the present invention provides an original process for the preparation of the desired enantiomers of formula (III) having the absolute configuration (1R), and more particularly of (+)-methyl (1R)-2-pentyl-2-cyclopentene-1-acetate.

As the strong peracid used according to the invention in the preparation of epoxides of formula (I), one can use organic peracids which are strongly electron-attracting, chosen amongst the peroxyacids of current use in oxidation reactions (see, for example, chapter III in Org. Chem., 5, ed. W. S. Trahanovsky, Academic Press, 1978). In this context, permaleic acid, perphthalic acid, m-chloroperbenzoic acid or yet the peracids of formula $CX_3COO_2H$, wherein X typically stands for a halogen atom, in particular chlorine or fluorine, can be cited as preferred agents. Preferably, permaleic or trifluoroperacetic acid will be used.

As appropriate solvents in this process, a chlorinated solvent will be preferably used. Very useful results have been obtained in particular with dichloromethane.

The esters of formula (III) used as starting products in the process described above are novel compounds, which are also an object of the invention. Amongst these esters, one can cite in particular (+)-methyl (1R)-2-pentyl-2-cyclopentene-1-acetate, the conversion of which, according to the present invention, allows the preparation of the preferred isomer of Hedione®.

The invention also concerns an original process for the preparation of the esters of formula (III), starting from commercially available materials or products which can be prepared using current reactions. The reactions which characterize the preparation process of esters (III) are schematically represented hereinafter:

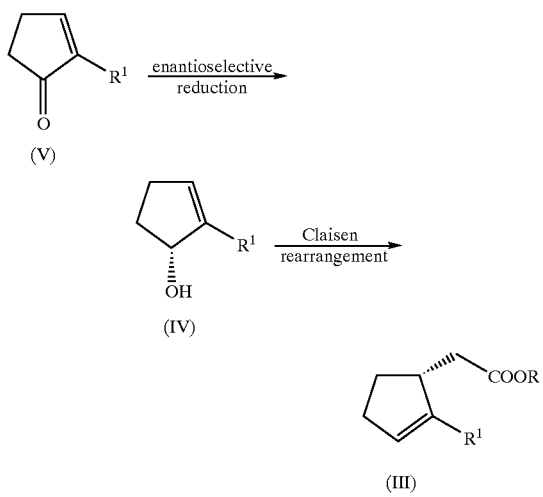

According to the invention, the first reaction in this scheme consists of an enantioselective reduction of the starting cyclopentenone which is carried out by means of a system of the oxazaborolidine-borane type, which, with respect to the substrate, can be used in stoichiometric or catalytic amounts. This is a system for the enantioselective reduction of ketones which is described in various publications (see, for example, E. J. Corey et al., J. Amer. Chem. Soc. 1987, 109, 7925; S. Itsuno et al., Bull. Chem. Soc. Jpn, 1987, 60, 395; D. J. Mathre et al., J. Org. Chem. 1991, 56, 751; V. K. Singh, Synthesis 1992, 605), but which, to our knowledge, has never been used in the reduction of cyclopentenones such as cited above. It involves the use of the oxazaborolidine of formula

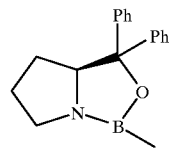

Ph = phenyl or (S)-tetrahydro-1-methyl-3,3-diphenyl-1H,3H-pyrrolo[1,2-c][1,3,2]oxazaborole as catalyst for the reduction, said reduction being effected using $BH_3$ (in complexed form). The reduction reaction delivers, further to the desired alcohol (IV), (S)-α,α-diphenyl-2-pyrrolidinemethanol, which can be isolated and re-converted into the oxazaborolidine mentioned beforehand, in a way known per se (see D. J. Mathre, ref. cited).

According to a more advantageous embodiment, the above-mentioned oxazaborolidine is used in catalytic amounts with respect to the cyclopentenone (V), to give the alcohols (IV) having an optical purity of at least 90% e.e. The detailed conditions of these reactions will be described further on.

We were also able to develop a new catalyst for the above-mentioned reduction according to the following formula

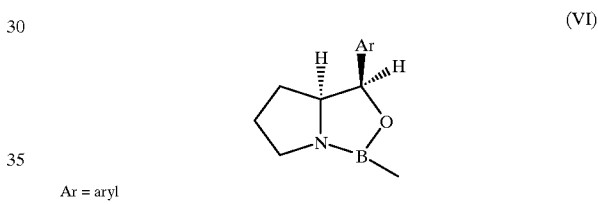

Ar = aryl in which, in comparison to the known oxazaborolidine catalyst described above, one of the phenyl groups is replaced by a hydrogen atom. In the above formula, the aryl substituent may be an unsubstituted or substituted phenyl group, like toluene, xylene, di-tert-butylbenzene or mesitylene, or even a fused aryl group, like naphthalene.

The new catalyst can be synthesized via a reaction which is analogous to that for the preparation of the known oxazaborolidine catalyst carrying two phenyl groups, which reaction uses, as starting product, the aminoalcohol of the following formula

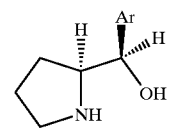

wherein Ar has the meaning indicated above. The aminoalcohols are prepared according to a known process (see. A. Ookawa, K. Soai, J. Chem. Soc. Perkin Trans. 1, 1987, 1465) and reacted with trimethylboroxine $(BOMe)_3$ to yield the desired catalyst.

These catalysts are new chemical entities which are also an object of the invention.

When using this new catalytic system with Ar=phenyl, namely (S)-tetrahydro-1-methyl-3-phenyl-1H,3H-pyrrolo

[1,2-c][1,3,2]oxazaborol, in the enantioselective reduction according to the present invention, we obtained results which were as good as those obtained with the known oxazaborolidine cited previously. As the latter, the new catalysts can be used in stoichiometric or catalytic amounts with respect to the cyclopentenone (V).

One further synthetic way to enantioselectively reduce the cyclopentenones of formula (V) into alcohols (IV) is a process involving a biotechnological step. Said ketones can be conventionally converted into the corresponding racemic acetates, and the latter then enantioselectively saponified into the desired optically active alcohols (IV) by means of a lipase.

Suitable lipases for this reaction step are known to a person skilled in the art and include for example *Candida antarctica, Pseudomonas fluorescens, Pseudomonas amano, Humicola lang, Candida cylindracea, Mucor miehei, Chromabacterium viscosum, Aspergillus niger, Mucor javanicus and Rhisopus arrhizus.*

The transformation of the keto function into an acetate function can be effected using agents of current use in the art. One can cite in this context the system $LiAlH_4$/acetic anhydride, but other systems can be used. Likewise, other esters besides the acetate may be used in the process.

The Claisen rearrangement of the allylic alcohols (III) made it possible to obtain the esters of formula (III) with total retention of the enantiemeric configuration. This is quite a surprising result, given the fact that one would have expected a considerable degree of racemization of the starting cyclopentenol via reversible dehydration, which is favored by the acidic conditions and the elevated temperature of the reaction medium. Yet, we observed practically no loss (less than 1% racemization) in the optical purity of the obtained product, relative to that of the starting cyclopentenol.

The conditions of these esterification reactions are described in further detail below.

In summary, the present invention allows the preparation of new optically active compounds which are themselves useful for the preparation of precious perfuming ingredients and which allow the preparation of the latter in very useful yields and with excellent diastereochemical and enantiomeric purities. And this, by making use of reactions which can be applied on an industrial scale, without danger for the environment.

The invention will now be described in greater detail by means of the following examples, in which the temperatures are indicated in degrees centigrade and the abbreviations have the usual meaning in the art.

EMBODIMENTS OF THE INVENTION

EXAMPLE 1

Preparation of (+)-(1R)-2-pentyl-1-cyclopenten-1-ol

A solution of 2-pentyl-2-cyclopenten-1-one (9.12 g, 60 mmole) in 140 ml of tetrahydrofurane (THF) was treated with an oxazaborolidine represented above, namely (S)-tetrahydro-1-methyl-3,3-diphenyl-1H,3H-pyrrolo[1,2-c][1,3,2]oxazaborole (16.7 ml; 0.36 M in toluene, 6.0 mmole; see D. J. Mathre, ref. cited). A solution of $BH_3.S(CH_3)_2$ (3.30 ml=2.64 g, 34.8 mmole) in THF (60 ml) was added dropwise at 0° over 1 h. The reaction was stopped with 3 ml of methanol (development of $H_2$), followed by ethyl ether and 5% HCl. The organic phase, which had been washed to neutrality (2× with water and 1× with brine), was separated and the solvent evaporated. 9.5 g of a crude product were obtained, which was distilled in a bulb-to-bulb apparatus (oven temp. 60°/11 Pa), to give 8.1 g of (+)-(1R)-2-pentyl-2-cyclopenten-1-ol (yield 89%).

The compound showed the following analytical data.

$[\alpha]^{20}_D$=+28.3 (c=2.7; $CHCl_3$) enantiomeric excess (e.e.)= 91% (measured on a chiral column of type Megadex®5 or CD-Chirasil® DEX CB on the basis of the corresponding trimethylsilyl ether) NMR($^1$H, 360 MHz): 0.89(t, J=7, 3H); 1.20–1.40(m, 4H); 1.40–1.57(m, 3H; with $D_2O$=2H); 1.69 (m, 1H); 2.02–2.47(m, 5H); 4.64(broad, 1H); 5.53(broad s, 1H) δ ppm. NMR($^{13}$C): 146.7(s); 126.9(s); 78.9(d); 34.1(t); 31.9(t); 29.7(t); 28.1(t); 27.5(t); 22.6(t); 14.1(q) δ ppm. MS: 154($M^+$, 2), 97(30), 83(100), 79(12), 67(7), 55(11), 41(9).

When using a different oxazaborolidine, namely (S)-tetrahydro-1-methyl-3-phenyl-1H,3H-pyrrolo-[1,2-c][1,3,2] oxazaborol (see Example 7), as catalyst in the asymmetric reduction, and in an amount of 10% relative to the substrate, the same chiral cyclopentenol was obtained in a yield of 68% and an e.e. of 90%.

EXAMPLE 2

Preparation of (+)-ethyl (1R)-2-pentyl-1-cyclopentene-1-acetate

A mixture of the cyclopentenol obtained according to Example 1 (5 g, 32.5 mmol) with triethyl orthoacetate (47.2 ml=42.1 g, 260 mmole, 8 eq.) was heated to 145° (temp. of oil bath 160°) under a nitrogen current in a reactor which was equipped with a Vigreux column and a condenser, while adding continuously, over 4 h, pivalic acid (232 mg, 2.28 mmole, 7 mol %) in triethyl orthoacetate (5.9 ml=5.26 g, 32.5 mmole, 1 eq.). During the reaction, the formed ethanol, as well as the ethyl acetate and a little orthoacetate, were removed by distillation. The reaction mixture was heated for 1 more hour, then cooled to 20°, hydrolyzed with diluted aqueous $NaHCO_3$ and extracted with ether. The organic layer was washed 2× with water and once with brine, dried over $Na_2SO_4$ and evaporated, to give 15.4 g of crude product. After distillation of the heads (6.6 g, 50°/1.1×10$^2$ Pa), 5.30 g (95°/1.1×10$^2$ Pa) of (+)-ethyl (1R)-2-pentyl-2-cyclopentene-1-acetate were obtained (yield 73%), having an enantiomeric purity of 90% e.e. (chiral column of the type Megadex®5).

$[\alpha]^{20}_D$=+23.6 (c=3.9 ; $CHCl_3$)

NMR($^1$H, 360 MHz): 0.89(t, J=7, 3H); 1.26(t, J=7, 3H); 1.22–1.63(m, 7H); 1.86–2.36(m, 6H); 2.53(dd, J=15 and 4, 1H); 2.95(broad, 1H); 4.14(q, J=7, 2H); 5.37(broad s, 1H) δ ppm.

NMR($^{13}$C): 14.1(q); 14.3(q); 22.6(t); 27.4(t); 28.9(t); 30.4 (t); 30.5(t); 31.8(t); 38.8(t); 43.7(d); 60.2(t); 124.3(d); 146.3 (s); 173.4(s) δ ppm.

MS: 224($M^+$, 24), 176(5), 150(31), 136(68), 121(20), 107(30), 93(56), 80(100), 79(92), 67(58), 55(18), 41(46), 29(63).

EXAMPLE 3

Preparation of (+)-methyl (1R)-2-pentyl-2-cyclopentene-1-acetate

The cyclopentenol previously described was reacted in a similar way to that described in Example 2, but using trimethyl orthoacetate (27 eq.) and 10 mole-% of pivalic acid. The reaction was run at a temperature of about 115° over a time of about 6 h. After the usual treatment, the desired (+)-methyl (1R)-2-pentyl-2-cyclopentene-1-acetate was obtained in 43% yield and with an enantiomeric purity of 90% e.e. (chiral column Megadex®5).

The compound showed the following analytical characteristics:

$[\alpha]^{20}_D$=+25.3 (c=3.6; CHCl$_3$)

NMR($^1$H, 360 MHz): 0.89(t, J=7, 3H); 1.20–1.60(m, 7H); 1.85–2.35(m, 6H); 2.54(dd, J=15 and 4, 1H); 2.93(broad, 1H); 3.67(s, 3H); 5.37(broad s, 1H) δ ppm.

NMR($^{13}$C): 14.1(q); 22.6(t); 27.4(t); 28.9(t); 30.4(t); 30.5 (t); 31.8(t); 38.5(t); 43.6(d); 51.5(q); 124.4(d); 146.2(s); 173.8(s) δ ppm.

MS: 210(M$^+$, 32), 178(3), 150(16), 136(59), 121(13), 107(23), 93(43), 80(100), 67(42), 41(36), 29(31).

This ester was also prepared, in an identical chemical and optical purity, by trans-esterification of its homologue, described in Example 2 (yield 85%), or saponification of the said homologue to form the corresponding acid, which was then esterified (global yield 85% ; conventional conditions).

The intermediate (+)-(1R)-2-pentyl 2-cyclopentene-1-acetic acid (yield 89%) showed an enantiomeric purity of 90% e.e. and the following analytical data:

$[\alpha]^{20}_D$=+32.5 (c=6.0 ; CHCl$_3$) NMR($^1$H, 360 MHz): 0.89(t, J=7, 3H); 1.20–1.65(m, 7H); 1.86–2.36(m, 6H); 2.60(dd, J=15,5 and 4, 1H); 2.95(broad, 1H); 5.39(broad s, 1H); ~10.3–11.3(broad, 1H) δ ppm.

NMR($^{13}$C): 14.1(q); 22.6(t); 27.4(t); 28.9(t); 30.4(t); 30.5 (t); 31.8(t); 38.5(t); 43.4(d); 124.6(d); 146.0(s); 180.2(s) δ ppm.

MS: 196(M$^+$, 31), 136(56), 125(10), 121(12), 107(20), 93(49), 91(41), 79(100), 77(62), 67(40), 53(21), 41(48), 29(39).

EXAMPLE 4

Preparation of (+)-methyl (1R,2S,3R)-2,3-epoxy-2-pentyl-1-cyclopentaneacetate

A solution of the ester described in Example 3 (2.10 g, 10.0 mmole) and maleic anhydride (1.46 g, 15.0 mmole, 1.5 eq.) in CH$_2$Cl$_2$ (15 ml) was treated dropwise, at 10°, with 70% H$_2$O$_2$ (0.58 g, 12 mmole, 1.2 eq.). After 4 h at 10°, the reaction mixture was poured into an aqueous saturated solution of NaHCO$_3$. The product was extracted with ether, washed with water and with brine, dried over Na$_2$SO$_4$ and evaporated to give 2.35 g of crude product. Distillation in a bulb-to-bulb-apparatus (oven temp. 70°/8 Pa) gave the epoxide in a pure state (1.95 g, 86%), with a diastereomeric excess d.e. of 100% and an enantiomeric purity of 90% e.e. (column Megadex®5). An identical result was obtained when 70% H$_2$O$_2$ (360 mg, 7.5 mmole) was used, added to a solution of (CF$_3$CO)$_2$O (2.31 g=1.53 ml, 11.0 mmole) in CH$_2$Cl$_2$ (20 ml) at 20°. After 30 min, this solution was added dropwise, at −50°, to a suspension of the ester described in Example 3 (1.05 g, 5.0 mmole) and of Na$_2$CO$_3$ (1.59 g, 15 mmole) in CH$_2$Cl$_2$ (10 ml). After the addition had been finished (15 min), the reaction was completed. The solution was treated as described above and the product distilled to give 863 mg (yield 76%) of pure (+)-methyl (1R,2S,3R)-2, 3-epoxy-2-pentyl-1-cyclopentaneacetate, showing characteristics which were identical to those cited above.

$[\alpha]^{20}_D$=+13.3 (c=3.7 ; CHCl$_3$)

NMR($^1$H, 360 MHz): 0.89(t, J=7, 3H); 1.11(m, 1H); 1.22–1.40(m, 6H); 1.48–1.66(m, 2H); 1.76–1.91(m, 2H); 1.95(dd, J=14 and 8, 1H); 2.22–2.38(m, 2H); 2.60(dd, 15,5 and 4, 1H); 3.29(s, 1H); 3.66(s, 3H) δ ppm.

NMR($^{13}$C): 14.0(q); 22.6(t); 24.7(t); 26.5(t); 26.7(t); 29.2 (t); 31.9(t); 34.5(t); 37.6(d); 51.6(q); 62.6(d); 68.3(s); 173.6 (s) δ ppm.

MS: 226(M$^+$, 3), 211(12), 183(26), 167(35), 152(42), 138(22), 123(37), 109(51), 96(89), 81(100), 67(56), 55(72), 41(88), 29(49).

Moreover, other reaction conditions were also used. The table hereinafter summarizes and compares the above-described results to those obtained by varying the epoxidation conditions. The various compounds (absolute configurations) present in the reaction product (weight %), as well as their retention time on a column of the type DB-WAX [100° (3 min), then 30°/min], are indicated in the table.

TABLE I

| Run | Reaction conditions | \[structure: cyclopentene with COOCH₃ chain\] (5737) | \[spiro epoxide with COOCH₃\] (659) | \[spiro epoxide diastereomer with COOCH₃\] (668) | \[bicyclic lactone with OH\] (1024) | \[bicyclic lactone with OH, diastereomer\] (1302) |
|---|---|---|---|---|---|---|
| 1 | $(CF_3CO)_2O/H_2O_2/$ $Na_2CO_3/CH_2Cl_2/-50°$ |  |  |  |  |  |
|  | 10 min | — | 97 | — | 1 | — |
|  | extr. | — | 91 | — | 2 | 1 |
| 2 | maleic anhydride/ $H_2O_2/CH_2Cl_2/10°$ |  |  |  |  |  |
|  | 2 h | 32 | 58 | 1 | — | 6 |
|  | 4 h; extr. | — | 84 | — | 1 | 10 |
| 3 | maleic anhydride/ $H_2O_2$/toluene/10→30° |  |  |  |  |  |
|  | 1 h | 3 | 77 | 6 | — | 5 |
|  | 4 h extr. | 1 | 80 | 1 | — | 9 |
| 4 | HCOOH/HCOONa/ $H_2O_2/40°$ |  |  |  |  |  |
|  | 6 h | 72 | 21 | 4 | not det. |  |
| 5 | m-chloroperbenzoic acid/$CH_2Cl_2/0°$ |  |  |  |  |  |
|  | 15 min | — | 83 | 14 | — | — |
|  | extr. |  |  |  |  |  |
| 6 | $CH_3CO_3H/CH_2Cl_2/20°$ |  |  |  |  |  |
|  | 1 h | 4 | 80 | 9 | — | — |
|  | 2 h | 1 | 78 | 12 | — | — |
|  | extr. | — | 83 | 12 | — | — |

EXAMPLE 5

Preparation of (+)-ethyl (1R,2S,3R)-2-epoxy-2-pentyl-1-cyclopentaneacetate

Tis epoxide was prepared under conditions similar to those described in Example 4, but starting from the ester described in Example 2. The table below summarizes the results obtained under the different reaction conditions.

time with brine, dried over $Na_2SO_4$ and the solvent evaporated to give 1.09 g of crude product. Distillation of the latter in a bulb-to-bulb apparatus (oven temp. (60–85°/7×10² Pa) gave 824 g of (+)-(1R)-cis-Hedione® with a purity of 80% (yield 66%, 87% d.e., 90% e.e.). A second fractional distillation gave the (+)-(1R)-cis-Hedione® containing 5 weight % of the isomer of (−)-(1S)-trans configuration, as well as 5

TABLE II

| | | Products (%) | | |
|---|---|---|---|---|
| | | 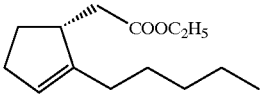 | 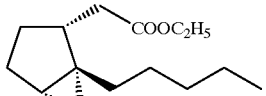 | 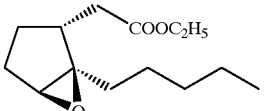 |
| Run | Reaction conditions | | | |
| 1 | $(CF_3CO)_2O/H_2O_2/$<br>$Na_2CO_3/CH_2Cl_2/-50°$<br>10 min | — | 91 | — |
| 2 | maleic anhydride/<br>$H_2O_2/CH_2Cl_2/10°$<br>2 h | — | 82 | — |
| 3 | m-chloroperbenzoic<br>acid/$CH_2Cl_2/0°$<br>15 min<br>extr. | — | 77 | 13 |
| 4 | $CH_3CO_3H/CH_2Cl_2/20°$<br>1 h<br>2 h | 3<br>1 | 83<br>84 | 12<br>— |

| | | Products (%) | |
|---|---|---|---|
| | | 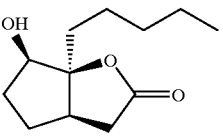 | 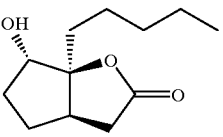 |
| Run | Reaction conditions | | |
| 1 | $(CF_3CO)_2O/H_2O_2/$<br>$Na_2CO_3/CH_2Cl_2/-50°$<br>10 min | — | — |
| 2 | maleic anhydride/<br>$H_2O_2/CH_2Cl_2/10°$<br>2 h | 1 | 11 |
| 3 | m-chloroperbenzoic<br>acid/$CH_2Cl_2/0°$<br>15 min<br>extr. | — | — |
| 4 | $CH_3CO_3H/CH_2Cl_2/20°$<br>1 h<br>2 h | —<br>— | —<br>11 |

EXAMPLE 6

Preparation of (+)-methyl (1R)-cis-3-oxo-2-pentyl-1-cyclopentaneacetate or (+)-(1R)-cis-Hedione®

A mixture of the epoxide described in Example 4 (1.0 g, 4.42 mmole), 4 Å molecular sieve (0.50 g) and toluene (10 ml) was treated at 23° with trifluoroboron etherate $BF_3.OEt_2$ (56 μl=63 mg, 0.44 mmole, 0.1 eq.). After 8 min at 20–25°, the reaction was stopped by adding a saturated, aqueous, icy solution of sodium bicarbonate, then the product was extracted with ether, washed two times with water and one weight % of a diene, i.e. methyl (2-pentyl-2-cyclopenten-1-ylidene) acetate.

When, in the same procedure, stoichiometric amounts of $BF_3.OEt_2$ were used, the (+)-(1R)-cis-Hedione® was obtained with 90% purity (90% d.e., 90% e.e.), in 70% yield.

Moreover, other reaction conditions, distinct from those previously mentioned were used in analogous manner. The table below summarizes and compares the above-mentioned results to those obtained under different reaction conditions. The different compounds (absolute configurations) present in the reaction product (weight %), as well as their retention time on a column of the type DB-WAX (100° (3 min), then 30°/min) are indicated in the table.

TABLE III

| Run | Reaction conditions | Compounds (% by weight) | | | | Starting epoxide |
|---|---|---|---|---|---|---|
| | | (748) [keto-diester cyclopentanone] | (730) [keto-diester cyclopentanone isomer] | (670) [diene ester] | (1024) [bicyclic lactone] | |
| 1 | AlCl₃ (0.1 eq.), CH₂Cl₂, 5° 10 min | 86 | 6–7 | 5 | 2 | — |
| 2 and 3 | BF₃·OEt₂ (1 eq.), tol., 20° 10 min | 88 | 4 | 8 | — | — |
| | a) 4 Å molecular sieve (50%) b) BF₃·OEt₂ (0.1 eq.), tol., 20° 5 min | 82 | 6 | 9 | 2 | — |
| 4 | MgI₂ (1 eq.), tol, 110° 10 min | 60 | 2 | 16 | — | — |
| 5 | Filtrol @ G24 (10%) tol., 110° 30 min | 56 | 5 | 9 | 20 | — |
| 6 | Sc(OSO₂CF₃)₃ (0.5 eq.), CH₂Cl₂, 20° 15 min | 78 | 6 | 7 | 9 | 0 |
| 7 | MgBr₂, tol., 110° 3 h. | 1 | — | — | 1 | 88 |
| 8 | LiClO₄, Et₂O, 5° 24 h | 24 | — | 23 | 23 | 28 |
| 9 | LiClO₄, tol., 24° 63 h | 54 | 1 | 23 | 5 | 5 |
| 10 | MgClO₄, tol., 50° 1 h | 31 | — | 34 | — | 35 |

EXAMPLE 7

Preparation of (S)-tetrahydro-1-methyl-3-phenyl-1H,3H-pyrrolo[1,2-c][1,3,2]oxazaborol A solution of (1R,2'S)-1-phenyl-2'-pyrrolidinemethanol (obtained according to Ookawa et al., ref. cited) (0.554 g, 3.1 mmol) and trimethylboroxine (0.226 g, 2.1 mmol) in toluene (10 ml) was stirred at 25° C. After 45 min, the solution was slowly warmed up to reflux during 2 h and $H_2O$ and the boronic acid formed were distilled off as an azeotropic mixture with toluene. Once the mixture was concentrated by half, fresh toluene (ca. 5 ml) was added (3 or 4 volumes of toluene needed to be added during the reaction). The reaction mixture was allowed to cool to room temperature overnight and the solution of the desired oxazaborolidine (5.2 ml, ca. [0.59 M]) was transferred via syringe into a bottle and stored under argon. The solution could be used as such in the reduction reactions described above.

MS: 201($M^+$, 100), 200(94), 186(12), 172(92), 158(20), 130(42), 104(19), 91(78), 77(18), 70(18), 67(18), 51(13), 39(15).

Comparative Example

Process Described in WO 95/33735

A. Methyl 2-pentyl-2-cyclopentene-1-acetate was epoxidized under the conditions described in the above-cited document, Example 1 ($Na_2SO_4$, HCOOH, HCOONa, $H_2O_2$ at 70%, 40°, 6 h). After ether extraction and distillation in a bulb-to-bulb apparatus of the reaction product, there was obtained essentially the starting ester, as is apparent from table I presented above (see run 4), the yield in the desired epoxide being only ~20%.

B. c-Methyl 2,3-epoxy-2-pentyl-r-1-cyclopentaneacetate (obtained in an analogous way to that described in Example 4, but starting from racemic methyl 2-pentyl-2-cyclopentene-1-acetate) was reacted in a way analogous to that described in example 2 of WO 95/33735.

A mixture of 400 mg of the above-mentioned epoxide (1.80 mmole) and 19 mg of LiI (0.14 mmole) was placed in a bulb-to-bulb apparatus and heated to 190°. After 10 min, the black mixture was distilled in vacuo (8 Pa). The distillate (277 mg) consisted essentially of the starting epoxide (82% pure). The distillate was again combined with the residue (68 mg) and heated 30 min to 190°, cooled and distilled in a bulb-to-bulb apparatus (oven temp. 90°/8 Pa) to obtain 110 mg of distillate. Redistillation of this product (oven temp. 110°/11 Pa) gave 85 mg of a product having a purity of 90% and showing the following analytical data.

IR (neat): 2950, 2920, 2855, 1760, ~1735(shoulder), ~1705(shoulder), 1450, 1215, 1185 $cm^{-1}$.

NMR($^1H$, 360 MHz): 0.87(t, J=7, 3H); ~1.2–1.8(m, 12H); 1.90(m, 1H); 2.05(m, 1H); 2.28(dd, J=17,5 and 3,5, 1H); 2.51(m, 1H); 2.85(dd, J=17,5 and 10, 1H) δ ppm.

NMR($^{13}C$): 177.5(s); 98.3(s); 42.1(d); 39.4(t); 38.1(t); 37.1(t); 34.4(t); 32.1(t); 24.0(t); 23.9(t); 22.5(t); 14.0(q) δ ppm.

MS: 196($M^+$, 6), 167(6), 153(10), 140(17), 125(100), 97(70), 81), 71(26), 69(30), 55(50), 41(69).

These spectral data correspond to the lactone the structure of which was cited further above in the text.

I claim:

1. Epoxide of formula

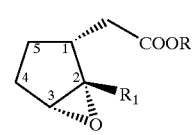

(I)

Having a cyclanic (1R) configuration, the group in position 2 being in a trans configuration and the epoxy group being in a cis configuration with respect to that in position 1 of the ring, and in which R represents a lower alkyl group and $R^1$ represents a saturated or unsaturated, linear or branched hydrocarbon group having from 1 to 8 carbon atoms.

2. (+)-Methyl (1R,2S,3R)-2,3-epoxy-2-pentyl-1-cyclcopentaneacetate.

3. A process for preparation of an epoxide of formula, (I)

having a cyclanic (1R) configurations the group in position 2 being in a trans configuration and the epoxy group being in a cis configuration with respect to that in position 1 of the ring, and in which R represents a lower alkyl group and $R^1$ represents a saturated or unsaturated, linear or branched hydrocarbon group having from 1 to 8 carbon atoms, wherein an ester of formula (III)

having a cyclanic configuration (1R)-cis and in which the symbols R and $R^1$ have the meaning indicated in formula (I), is reacted with a strong peracid in an inert organic solvent.

4. Process according to claim 3, wherein the ester of formula (III) is obtained by a method which comprises the reduction of a ketone of formula (V)

in which $R^1$ has the meaning indicated in formula (III), by means of $BH_3$ in the presence of a chiral oxazaborolidine, to provide a (1R) configuration cyclopentenol of formula

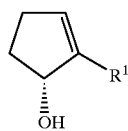

(IV)

which is then reacted with an appropriate alkyl orthoacetate, under reaction conditions favorable for a Claisen type rearrangement, to give the desired ester.

5. Process according to claim 4, wherein the ketone is reduced using a chiral oxazaborolidine according to formula

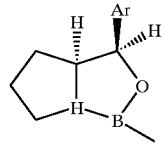

(VI)

in which Ar represents a substituted or unsubstituted phenyl group or a fused aryl group.

6. Process according to claim 3, comprising the reduction of (+)-methyl (1R)-2-pentyl-2-cyclopentene-1-acetate, to obtain (+)-methyl (1R,2S,3R)-2,3-epoxy-2-pentyl-1-cyclopentaneacetate.

7. Process according to claim 3, wherein the strong peracid is permaleic acid or trifluoroperacetic acid.

8. Process according to claim 4, wherein 2-pentyl-2-cyclopenten-1-one is reduced to give (+)-(1R)-2-pentyl-2-cyclopenten-1-ol.

9. Process according to claim 8, wherein said cyclopentenol is reacted with methyl orthoacetate in the presence of pyvalic acid to provide (+)-methyl (1R)-2-pentyl-2-cyclopentene-1-acetate.

10. Epoxide of formula

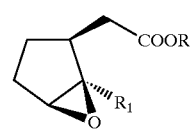

(I')

wherein the substituent groups epoxy and carboxy have a strictly cis configuration, R stands for a lower alkyl radical and $R^1$ stands for a hydrocarbon group, saturated or unsaturated, linear or branched, having from 1 to 8 carbon atoms.

* * * * *

UNITED STATES PATENT AND TRADEMARK OFFICE
CERTIFICATE OF CORRECTION

PATENT NO. : 5,962,706  Page 1 of 4
DATED : October 5, 1999
INVENTOR(S) : Charles Fehr It is certified that error appears in the above-identified patent and that said Letters Patent is hereby corrected as shown below:

On the title page at [57] ABSTRACT: change the formula to read as follows:

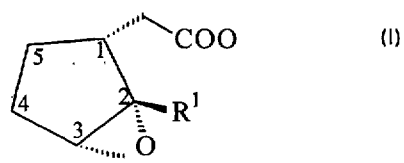

On the title page at [57] ABSTRACT, second-to-last line of text: change "opoxides" to --epoxides--.

Column 1: delete lines 6-26, beginning with "The new epoxides of formula" at line 6, and ending with "is also described." at line 26.

UNITED STATES PATENT AND TRADEMARK OFFICE
CERTIFICATE OF CORRECTION

PATENT NO. : 5,962,706
DATED : October 5, 1999
INVENTOR(S) : Charles Fehr

It is certified that error appears in the above-identified patent and that said Letters Patent is hereby corrected as shown below:

Column 1, lines 43-48: change the formula to read as follows:

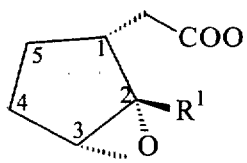 (I)

Column 2, line 25: change "epoxicle" to --epoxide--.

Column 3, lines 4-9: change the formula to read as follows:

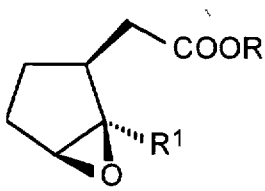 (I')

Column 10, line 14: change "20°" to --0°--.

UNITED STATES PATENT AND TRADEMARK OFFICE
CERTIFICATE OF CORRECTION

PATENT NO. : 5,962,706
DATED : October 5, 1999
INVENTOR(S) : Charles Fehr

Page 3 of 4

It is certified that error appears in the above-identified patent and that said Letters Patent is hereby corrected as shown below:

Column 18, lines 4-9: change the formula to read as follows:

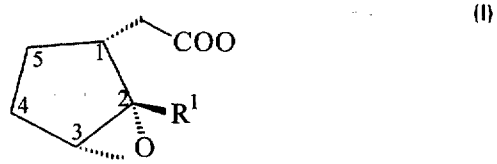
(I)

Column 18, line 13: change "Having" to --having--.

Column 18, line 21: change "cyclcopentaneacetate" to --cyclopentaneacetate--.

Column 18, lines 25-30: change the formula to read as follows:

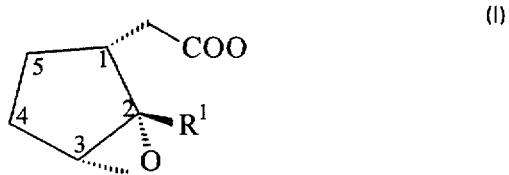
(I)

Column 18, line 33: change "configurations" to --configuration,--.

UNITED STATES PATENT AND TRADEMARK OFFICE
CERTIFICATE OF CORRECTION

PATENT NO. : 5,962,706
DATED : October 5, 1999
INVENTOR(S) : Charles Fehr

It is certified that error appears in the above-identified patent and that said Letters Patent is hereby corrected as shown below:

Column 20, lines 14-19: change the formula to read as follows:

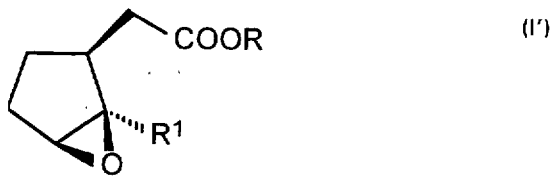

(I')

Signed and Sealed this

Twentieth Day of June, 2000

*Attest:*

Q. TODD DICKINSON

*Attesting Officer*   Director of Patents and Trademarks

UNITED STATES PATENT AND TRADEMARK OFFICE
CERTIFICATE OF CORRECTION

PATENT NO. : 5,962,706

DATED : October 5, 1999

INVENTOR(S) : Charles Fehr

Page 1 of 4

It is certified that error appears in the above-identified patent and that said Letters Patent is hereby corrected as shown below:

On the title page at [57] ABSTRACT: change the formula to read as follows:

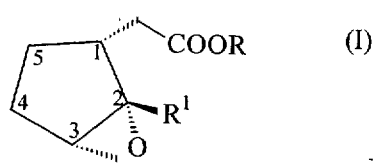

On the title page at [57] ABSTRACT, second-to-last line of text: change "opoxides" to --epoxides--.

Column 1: delete lines 6-26, beginning with "The new epoxides of formula" at line 6, and ending with "is also described." at line 26.

UNITED STATES PATENT AND TRADEMARK OFFICE
CERTIFICATE OF CORRECTION

PATENT NO. : 5,962,706
DATED : October 5, 1999
INVENTOR(S) : Charles Fehr

It is certified that error appears in the above-identified patent and that said Letters Patent is hereby corrected as shown below:

Column 1, lines 43-48: change the formula to read as follows:

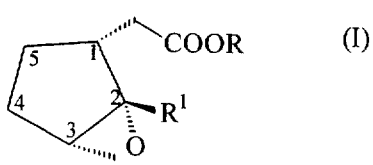

Column 2, line 25: change "epoxicle" to --epoxide--.

Column 3, lines 4-9: change the formula to read as follows:

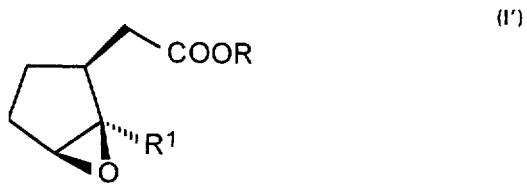

Column 10, line 14: change "20°" to --0°--.

UNITED STATES PATENT AND TRADEMARK OFFICE
CERTIFICATE OF CORRECTION

PATENT NO. : 5,962,706
DATED : October 5, 1999
INVENTOR(S) : Charles Fehr

It is certified that error appears in the above-identified patent and that said Letters Patent is hereby corrected as shown below:

Column 18, lines 4-9: change the formula to read as follows:

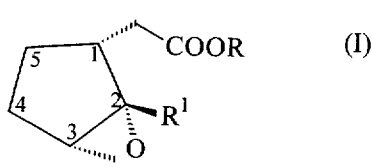

Column 18, line 13: change "Having" to --having--.

Column 18, line 21: change "cyclcopentaneacetate" to --cyclopentaneacetate--.

Column 18, lines 25-30: change the formula to read as follows:

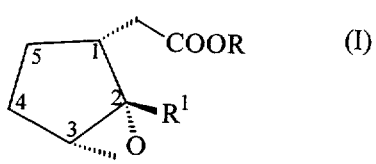

UNITED STATES PATENT AND TRADEMARK OFFICE
CERTIFICATE OF CORRECTION

PATENT NO. : 5,962,706
DATED : October 5, 1999
INVENTOR(S) : Charles Fehr

Page 4 of 4

It is certified that error appears in the above-identified patent and that said Letters Patent is hereby corrected as shown below:

Column 18, line 33: change "configurations" to --configuration,--.

Column 20, lines 14-19: change the formula to read as follows:

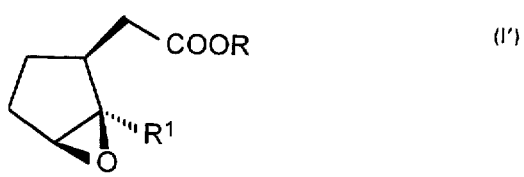

Signed and Sealed this

Nineteenth Day of December, 2000

Attest:

Q. TODD DICKINSON

Attesting Officer

Commissioner of Patents and Trademarks